United States Patent [19]

Mase et al.

[11] Patent Number: 4,505,805
[45] Date of Patent: * Mar. 19, 1985

[54] OXYGEN CONCENTRATION DETECTOR

[75] Inventors: Syunzo Mase, Aichi; Shigeo Soejima, Nagoya, both of Japan

[73] Assignee: NGK Insulators, Ltd., Japan

[*] Notice: The portion of the term of this patent subsequent to Oct. 4, 2000 has been disclaimed.

[21] Appl. No.: 383,223

[22] Filed: May 28, 1982

[30] Foreign Application Priority Data

Jun. 4, 1981 [JP] Japan ................... 56-84968

[51] Int. Cl.³ ............................................. G01N 27/46
[52] U.S. Cl. ..................... 204/425; 204/412; 204/426; 204/427; 219/505; 219/553
[58] Field of Search ................. 204/15, 412, 421–429; 422/98; 219/505, 553

[56] References Cited

U.S. PATENT DOCUMENTS

| 3,924,098 | 12/1975 | Dunn ................... 219/553 |
| 4,101,454 | 7/1978 | Kulwick et al. .......... 219/553 |
| 4,145,272 | 3/1979 | Nakamura . | |
| 4,167,163 | 9/1979 | Moder .................. 204/424 |
| 4,264,425 | 4/1981 | Kimura et al. .......... 204/425 |
| 4,265,724 | 5/1981 | Haecker . | |
| 4,293,838 | 10/1981 | Wahlers et al. ......... 219/553 |
| 4,298,573 | 11/1981 | Fujishiro .............. 204/426 |
| 4,300,991 | 11/1981 | Chiba et al. ........... 204/426 |
| 4,321,577 | 3/1982 | Carlson ................ 422/98 |
| 4,407,704 | 10/1983 | Mase et al. ........... 204/425 |

FOREIGN PATENT DOCUMENTS

| 30164 | 6/1981 | European Pat. Off. ..... 204/427 |
| 56-79246 | 6/1981 | Japan ..................... 204/428 |

Primary Examiner—T. Tung
Attorney, Agent, or Firm—Parkhurst & Oliff

[57] ABSTRACT

The disclosed oxygen concentration detector includes at least one oxygen concentration cell and at least one oxygen-ion-conducting solid electrolyte, and an alternating current of a specific frequency is applied to the oxygen concentration cell so as to raise the temperature thereof, while a direct current is applied to the oxygen-ion-conducting solid electrolyte so as to control the oxygen partial pressure at one or two electrodes of the oxygen concentration cell.

9 Claims, 23 Drawing Figures

FIG_14
PRIOR ART

FIG_15
PRIOR ART

FIG_16

FIG_17

OXYGEN CONCENTRATION DETECTOR

BACKGROUND OF THE INVENTION

1. FIELD OF THE INVENTION

This invention relates to an oxygen concentration detector which detects oxygen concentration in a gas by using an oxygen concentration cell made of an oxygen-ion-conducting solid electrolyte.

2. DESCRIPTION OF THE PRIOR ART

To measure the oxygen concentration in exhaust gas from internal combustion engines, oxygen concentration detectors made of oxygen-ion-conducting solid electrolyte and based on the principle of an oxygen concentration cell have been used. A typical example of such oxygen concentration detectors uses yttria-added zirconia porcelain as the solid electrolyte with platinum electrodes mounted thereon. Conventionally, the oxygen concentration detectors are used to control the air-fuel ratio $\lambda$ at 1.0. However, the fuel efficiency is high under lean burn conditions wherein air content is higher than that at the air-fuel ratio $\lambda$ of 1.0, while the output efficiency is high under rich burn conditions wherein air content is lower than that at the air-fuel ratio $\lambda$ of 1.0. In order to control the air-fuel ratio $\lambda$ at a level which is different from 1.0 for achieving a high fuel efficiency or a high output efficiency, it is necessary to accurately measure the electromotive force and the temperature of the oxygen concentration cell. Oxygen concentration detectors capable of simultaneous measurement of the temperature and the electromotive force are known; for instance, detectors using temperature sensing elements for measuring the temperature of the solid electrolyte, detectors using coiled heater wires disposed in the solid electrolyte for heating them, and detectors using both the temperature sensing elements and the coiled heater wires for effecting both the heating and temperature measurement of the solid electrolyte.

The oxygen concentration detectors of the prior art have shortcomings in that the temperature of the solid electrolyte exposed to the exhaust gas from an internal combustion engine is not uniform and the temperature measurement at one point thereof does not provide accurate picture of the temperature of solid electrolyte; that when the temperature of the exhaust gas is changed the output of the temperature sensing element has a time lag in detecting the temperature change of the solid electrolyte so that the temperature of the solid electrolyte cannot be measured accurately; that when the temperature of the oxygen concentration detector is low, the catalytic ability of platinum is reduced while the electric resistance of the solid electrolyte is increased and the impedance of the oxygen concentration detector becomes high, and the reduced catalytic ability and the high impedance tend to render the oxygen concentration detector susceptible to adverse effects of noises or the like and to reduce the response speed thereof; and that the structure of the oxygen concentration detectors are complicated. Thus, the conventional oxygen concentration detectors for the measurement of both the electromotive force and the temperature of the solid electrolyte are not practicable.

It has been proposed to apply a direct current to the oxygen concentration cell so as to shift the rapid change point of the electromotive force of the cell from a level corresponding to the above-mentioned air-fuel ratio $\lambda = 1.0$ to another level. However, such proposal has a shortcoming in that accurate measurement of oxygen concentration cannot be obtained because the polarization becomes excessively large at low temperatures and the fluctuation of the air-fuel ratio $\lambda$ with temperature is large.

SUMMARY OF THE INVENTION

Therefore, an object of the present invention is to obviate the above-mentioned shortcomings of the prior art by providing an improved oxygen concentration detector which has quick response at low temperatures and is capable of controlling the air-fuel ratio $\lambda$ at an arbitrary level. The oxygen concentration detector of the invention has a long service life and consumes only a small amount of electric power.

To fulfil the above-mentioned object, the oxygen concentration detector of the invention comprises a plurality of resistive bodies, each of said resistive bodies having a composition including a number of portions with a negative temperature coefficient of electric resistance and high-resistance substance layers separating said portions one from the other, and electrodes mounted on the composition, impedance of each said resistive bodies depending only on distributed constants of said composition for frequencies higher than a certain boundary frequency; at least two oxygen-ion-conducting solid electrolytes, each of said solid electrolytes being formed of one of said resistive bodies; at least one oxygen concentration cell formed of one of said solid electrolytes; an AC power source adapted to apply an alternating current to said cell so as to heat said cell, said alternating current having a frequency which is higher than said certain frequency; and a DC power source adapted to apply a direct current to the other oxygen-ion-conducting solid electrolyte which is not said oxygen concentration cell, so as to control the oxygen partial pressure at the electrode of said oxygen concentration cell.

Preferably, the impedance of the oxygen concentration cell is determined by measuring the magnitude of the alternating current of the above-mentioned frequency flowing through the oxygen concentration cell.

In the resistive bodies of the oxygen concentration detector, the above-mentioned portions with the negative temperature coefficient of electric resistance (to be referred to as NTCR hereinafter) can be in the form of fine grains or thin films.

Figure 6:
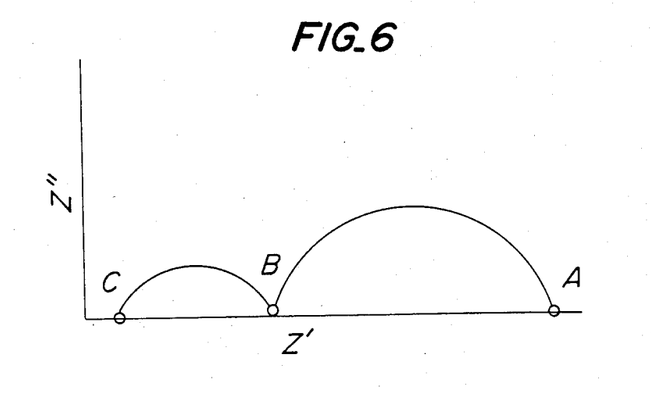
FIG. 6 is a graph showing the impedance characteristics of the resistive body.

Another object of the present invention is to provide an oxygen concentration detector for detecting oxygen concentration in gases, comprises a plurality of resistive bodies, each of said resistive bodies having a composition including a number of portions with a negative temperature coefficient of electric resistance and high-resistance substance layers separating said portions one from the other, and electrodes contacting said composition, at least one of said compositions being a solid electrolyte forming oxygen concentration cell, at least the other one of said composition being a solid electrolyte other than said oxygen concentration cell, a plurality of electrodes contacting said resistive bodies; an AC power source adapted to apply an AC current to said oxygen concentration cell so as to heat said cell, said AC power source being operable at AC frequencies which are not lower than a frequency whose complex impedance characteristics which when graphed in the manner shown in FIG. 6 hereof correspond to point B of said graphed complex impedance characteristics, a DC source adapted to apply a DC current to that solid electrolyte which does not form said oxygen concentration cell, so as to control the oxygen partial pressure around at least one electrode contacted said oxygen concentration cell, and means for measuring a DC potential difference of the oxygen concentration cell.

A further object of the present invention is to provide the detector wherein said portions with a negative temperature coefficient of electric resistance are fine grains.

A still further object of the present invention is to provide the detector wherein said portions with a negative temperature coefficient of electric resistance are thin films.

Another object of the present invention is to provide the detector wherein an AC current and an AC voltage between the electrode have a negative relation, in which one increases, the other decreases.

Another object of the present invention is to provide the detector wherein the AC current has a frequency at which an impedance of electrostatic capacitance $C_2$ at the highly resistant region layers interposed between the fine grains or the thin films is smaller than a resistance $R_2$ at the highly resistant region layers.

Another object of the present invention is to provide the detector further comprising means for detecting the impedance of selected one of said resistive bodies by applying an AC current thereto, said AC current having a frequency which is not lower than a frequency whose complex impedance characteristics which when graphed in the manner shown in FIG. 6 hereof correspond to point B of said graphed complex impedance characteristics.

Another object of the present invention is to provide the detector further comprising means for detecting the impedance of selected one of said resistive bodies by applying an AC current thereto, said AC current having a frequency which is not lower than a frequency whose complex impedance characteristics which when graphed in the manner shown in FIG. 6 hereof correspond to point B of said graphed complex impedance characteristics.

Another object of the present invention is to provide the detector further comprising an auxiliary heating means related selected one of said resistive body.

BRIEF DESCRIPTION OF THE DRAWINGS

For a better understanding of the invention, reference is made to the accompanying drawings, in which.

Throughout different views of the drawings, 1 is a cylindrical solid electrolyte with a bottom, 2 is a temperature sensing element, 3 is a coiled heater wire, 4 and 5 are electrodes, 6 is a fine grain having a negative temperature coefficient of electric resistance (NTCR), 7 and 7A are high-resistance layers, 8, 23, 24 and 26 are electrodes, 9 is a thin film with an NTCR, 10, 11, 22 and 25 are resistive bodies (solid electrolyte), 12 is a reference electrode, 13 is a measuring electrode, 14 is an outer electrode, 15 is an AC power source, 16 is a current-detecting resistor, 17 is a DC voltage detector, 18 and 21 are DC power sources, 19 is an AC voltage detector, 20 and 29 are shielding layers, 27 is a protective layer, 28 is a porous substance layer, 30 is cylindrical alumina ($Al_2O_3$) porcelain case, and 31 is a current-limiting resistor.

DESCRIPTION OF THE PREFERRED EMBODIMENTS

Figures 1, 2, 3, 4:
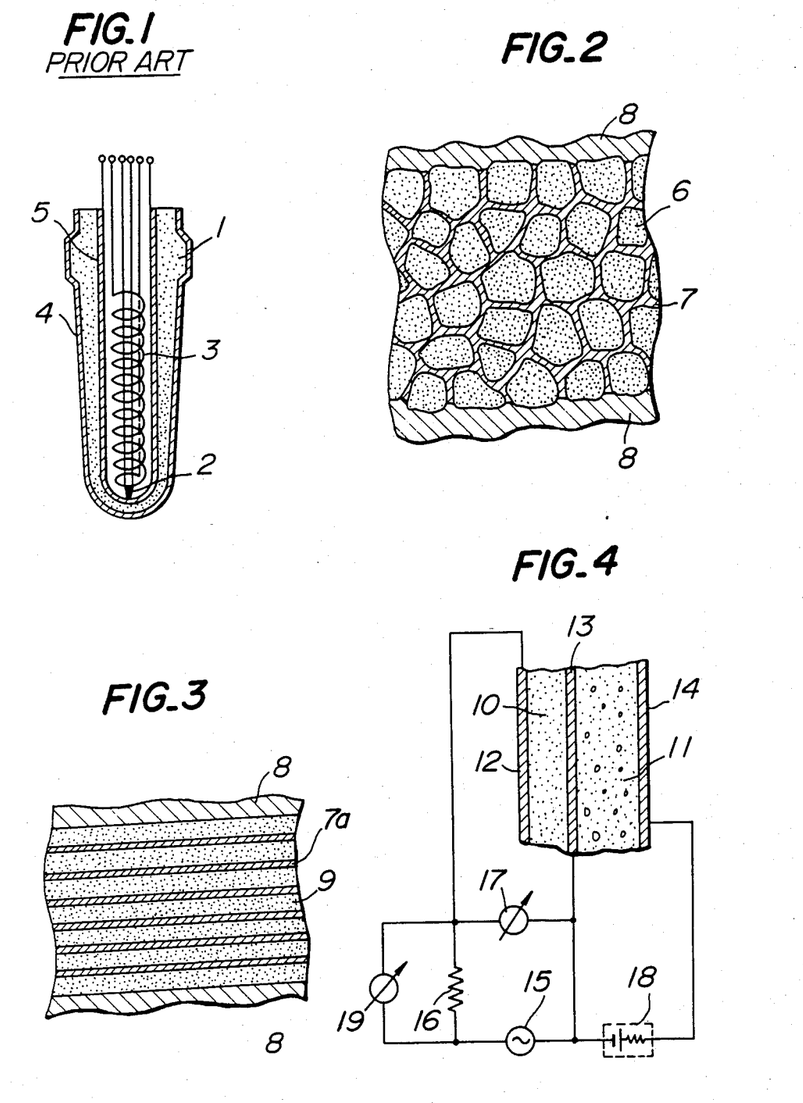
FIG. 1 is a schematic sectional view of an oxygen concentration detector of the prior art.
FIGS. 2 and 3 are fractional schematic sectional views of resistive bodies which are used in the oxygen concentration detector of the invention.
FIG. 4 is a diagrammatic illustration of an embodiment of the oxygen concentration detector according to the present invention.

Before entering the details of the invention, the prior art will be briefly reviewed. Referring to FIG. 1, a typical oxygen concentration detector for measuring both the electromotive force and the temperature of an oxygen concentration cell comprises a cylindrical oxygen ion conductive solid electrolyte 1 having a bottom end and a temperature sensing element 2 disposed therein for measuring the temperature of said solid electrolyte 1. Electrodes 4 and 5 are mounted on the outer and inner surfaces of the solid electrolyte 1, so as to measure the electromotive force thereacross. Some oxygen concentration detectors of the prior art have a coiled heater wire 3 disposed in the cylindrical solid electrolyte 1 for heating the electrolyte 1. Other concentration detectors of the prior art have both the temperature sensing element 2 and the coiled heater wire 3, so as to carry out both the heating of the solid electrolyte 1 and the measurement of the temperature thereof. Such oxygen concentrations detectors of the prior art have shortcomings in that the one-point measurement of the temperature is not very accurate in view of non-uniform temperature distribution in the solid electrolyte, that the temperature detection has a time lag when the exhaust gas temperature changes, that the oxygen concentration detectors are susceptible to adverse influences from noises at low temperatures, and that the physical structure thereof is complicated, as pointed out above.

The present invention obviate the shortcomings of the prior art.

FIG. 2 shows a fragmental schematic sectional view of a resistive body to be used in the oxygen concentration detector of the invention. The resistive body comprises fine grains 6 having a negative temperature coefficient of electric resistance and high-resistance substance layers 7 separating the fine grains one from the other. The fine grains 6 and the high-resistance substance layer 7 form a solid electrolyte 1, and the electrodes 8 made of gold or platinum are mounted on opposite end surfaces of the solid electrolyte 1. For instance, the composition of the resistive body i.e. oxygen ion conductive solid electrolyte body 1 is a ceramic material such as ceramics of zirconia ($ZrO_2$) porcelain, $\beta$-alumina ($\beta$-$Al_2O_3$) porcelain, aluminum nitride (AlN), titania ($TiO_2$) porcelain, zinc oxide (ZnO), tin oxide ($SnO_2$), or barium titanate ($BaTiO_3$); or a composition formed by binding fine grains of semiconductor such as metallic silicon (Si) with high-resistance glass or silicon oxide. In such composition, the fine grains 6 are formed of fine crystal grain of $ZrO_2$, $\beta$-$Al_2O_3$, AlN, $TiO_2$, ZnO, $SnO_2$, $BaTiO_2$, or Si, while the high-resistance substance layers 7 are formed of grain boundaries, such as glass, or silicon oxide. FIG. 3 shows a different microscopic structure of the resistive body, wherein the thin films 9 is made of material with negative temperature coefficient of electric resistance by a suitable method such as sputtering, chemical vapour deposition (CVD), or printing, which layers 9 correspond to the fine grains 6 of FIG. 2, and high-resistance substance layers 7A are formed so as to separate the above-mentioned films 9 having negative temperature coefficient of electric resistance one from the other.

FIG. 4 shows a schematic diagram of an embodiment of the oxygen concentration detector according to the present invention. Each of two resistive bodies 10 and 11 comprises a plurality of fine grains having negative temperature coefficiency of electric resistance and high-resistance substance layers separating the fine grains, and the two resistive bodies 10 and 11 are both oxygen-ion-conductive solid electrolyte made of zirconia ($ZrO_2$) porcelain. An oxygen ion conductive concentration cell is formed by mounting a reference electrode 12 and a measuring electrode 13 to the one resistive body 10, while the other resistive body 11 is tightly mounted on the measuring electrode 13 and an outer electrode 14 is attached to the opposite surface of the resistive body 11. Thus, the measuring electrode 13 acts as a common electrode for the two resistive bodies 10 and 11. An AC power source 15 is connected across the reference electrode 12 and the measuring electrode 13 through a current-detecting resistor 16. The power source 15 has such frequency that most of the AC polarization occur within the inside of the resistive body 10. A DC voltage detector 17 is connected across the resistive body 10, so as to measure the output voltage of the oxygen concentration cell. A DC power source 18 is connected across the outer electrode 14 and the measuring electrode 13, with the positive voltage applied to the outer electrode 14, so as to apply a direct current through the resistive body 11 of the illustrated embodiment. The resistive body 11 of the illustrated embodiment is porous. An AC voltage detector 19 is connected across the current-detecting resistor 16. The reference electrode 12 is exposed to the open atmosphere, while the outer electrode 14 is exposed to a gas to be measured.

In the oxygen concentration detector of the above-mentioned structure, the oxygen concentration cell made of the resistive body 10 is heated to a high temperature by the alternating current applied thereto, so that its performance at the start or cold state is improved. The direct current applied to the resistive body 11 acts to shift the oxygen ions in the resistive body 11, so that the oxygen density at the boundary between the resistive body 11 and the measuring electrode 13 is controlled, whereby that value of the air-fuel ratio $\lambda$ where the electromotive force of the oxygen concentration cell varies suddenly is shifted from 1.0 to the excess air (or lean burn) side or to the deficient air (rich burn) side. More particularly, oxygen in the gas being measured diffuses toward the measuring electrode 13 through the porous resistive body 11 at a diffusing speed proportional to the oxygen concentration difference across the opposite ends of the resistive body 11. The thus diffusing oxygen ionize at the boundary between the measuring electrode 13 and the resistive body 11 through the following reactions.

$$O_2 + 4e \rightarrow 2(O^{--})$$

The oxygen ions then move through the resistive body 11 until arriving at the outer electrode 14 where they are reconverted into oxygen gas and emitted therefrom. Accordingly, there is the following relationship between the oxygen concentration Co in the gas being measured and the oxygen concentration Ce at the boundary between the measuring electrode 13 and the resistive body 11.

$$Ce = Co - KI/nF.$$

Here, I represents the current density of the direct current flowing through the measuring electrode 13, K is a constant representing the diffusion resistance of the resistive body for oxygen gas, n is a charge number in the reaction at the electrode which charge number is 4 in this case, and F is the Faraday constant. As can be seen from the Nernst equation, the electromotive force of an oxygen concentration detector using the principle of the oxygen concentration cell varies suddenly for slight excess oxygen or slight excess fuel in the atmosphere of nearly zero (0) oxygen concentration Ce at the boundary between the measuring electrode 13 and the solid electrolyte 11. It is noted that the oxygen concentration Ce at the above-mentioned boundary can be made zero at an arbitrary value of the oxygen concentration Co in the gas being measured, by selecting such values of the constants K and I which render KI/nF = Co. Since the electromotive force of the oxygen concentration cell varies suddenly when the oxygen concentration Ce at the above-mentioned boundary is zero, an arbitrary oxygen concentration in the exhaust gas, which oxygen concentration is different from that at the air-fuel ratio $\lambda = 1.0$, can be now detected accurately and easily by regulating the values of K and I.

The porous resistive body 11 is heated by the heat generated in the oxygen concentration cell 10, so that carbon and other substances in the gas being measured hardly deposit in the resistive body 11, and the oxygen diffusion speed in the resistive body 11 is not affected by deposition of carbon or the like. Besides, the impedance of the resistive body 11 is reduced to an extremely small value by the above-mentioned heating, so that the voltages across the boundaries between the resistive body 11 and the electrode 13 and between the resistive body 11 and the electrode 14 are low, and the electrodes 14 are low, and the electrodes 13 and 14 are free from chipping even after a long period of operation. It is noted that, if the polarity of the DC power source 18 of FIG. 4 is reversed, the oxygen concentration at the measuring electrode 13 is raised, while the oxygen concentration at the outer electrode 14 is reduced. With the thus reversed distribution of the oxygen concentration, that value of the air-fuel ratio λ where the electromotive force of the oxygen concentration cell varies suddenly is shifted to the deficient air (rich burn) side.

When the polarity of the DC power source 18 is reversed, it is also possible to use the measuring electrode 13 as a kind of reference electrode with 100% oxygen concentration, so that the reference electrode 12 of FIG. 4 may be exposed to a gas being measured so as to detect the oxygen concentration thereof. In any case, the direct current from the DC power source 18 is applied only to the resistive body 11 but not to the oxygen concentration cell 10, so that the direct current does not affect the DC electromotive force of the oxygen concentration cell 11.

In the heating of the resistive body according to the present invention, an AC power source with that frequency which causes the AC polarization to occur mainly in the inside of the resistive body is used. The reason for using such AC frequency will be explained now.

Figure 5:
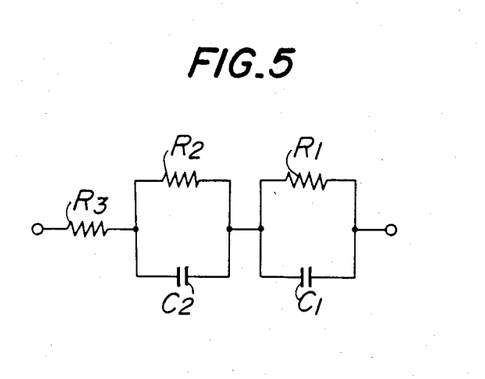
FIG. 5 is an equivalent circuit diagram of the resistive body.

FIG. 5 shows an electrical equivalent circuit of the resistive body having electrodes as shown in FIG. 2 or FIG. 3, which resistive body includes the above-mentioned fine grains or thin films with an NTCR and high-resistance substance layers separating the fine grains or thin films one from the other. In the equivalent circuit of FIG. 5, $R_1$ is a polarization resistance component at the boundary between the electrode and the resistive body, $C_1$ is an electrostatic capacitance component due to the polarization at the boundary between the electrode and the resistive body, $R_2$ is a resistance component at the high-resistance substance layer 7 or 7A between the NTCR fine grains 6 or thin films 9, $C_2$ is an electrostatic capacitance component of the high-resistance substance layer 7 or 7A, and $R_3$ is a resistance component of the NTCR fine grain 6 or thin film 9. The frequency characteristics of the complex impedance $Z = Z' - jZ''$ of the resistive body, as represented by the equivalent circuit of FIG. 5, includes two continuous arcuate portions as shown in FIG. 6. In FIG. 6, the resistance value of point A corresponds to the sum of the three resistance components $R_1 + R_2 + R_3$ of FIG. 5, the resistance value of point B corresponds to the sum of the two resistance components $R_2 + R_3$, and the resistance value of point C corresponds to the resistance component $R_3$. The polarization of the resistive body from the point A to the point B on the frequency characteristics curve of FIG. 6 is mainly due to the resistance component $R_1$ and the capacitance component $C_1$, and that from the point B to the point C is mainly due to the resistance components $R_2$, $R_3$ and the capacitance component $C_2$. As regards the variation of the complex impedance characteristics with the frequency variation, the point A represents DC, and as the frequency increases, the complex impedance characteristics varies along the arcuate locus toward the point B and further along the other arcuate locus toward the point C.

The arcuate characteristics from the point A to the point B of FIG. 6 varies considerably depending on the surface conditions of the resistive body, on the manner in which the electrodes are mounted on the resistive body, and on the time length of using the resistive body. Accordingly, if an AC voltage of a frequency in the range between the points A and B is used, it is difficult to apply electric power necessary for the heating in a stable fashion. When the resistive body is designed for use at a high temperature and electrodes of refractory materials such as platinum electrodes are used, or when solid electrolyte is used as the resistive body, the arcuate locus between the points A and B of FIG. 6 generally becomes very large at low temperature. Accordingly, if the frequency in the range between the points A and B is used in such cases, high voltages are generated at the boundaries between the electrodes and the resistive body, and such high voltages tend to cause chipping of the electrodes, chemical decay of the resistive body surface, electric discharges, induction interferences, and other adverse effects.

On the other hand, in the heating of the resistive body according to the present invention, an AC current of that frequency which generates polarization mainly in the inside of the resistive body, i.e., the frequency higher than that for the point B of FIG. 6, is applied to the resistive body. Thus, even when the AC current is large enough for heating the resistive body, no chipping of the electrodes and no chemical decay and no breakage of the resistive body are caused. The reason for the elimination of the electrode chipping and the electrolyte decay appears to be in that, when an AC voltage with a frequency higher than that for the point B of FIG. 6 is applied to the resistive body, most of the polarization occurs in the composition of the resistive body represented by the components $R_2$, $C_2$, and $R_3$ collectively designating the distributed constants thereof, and the polarization within the resistive body is uniformly distributed in the direction of the thickness thereof, whereby chemical change or decay due to electric current therethrough hardly occur. Furthermore, at the boundaries between the electrodes and the resistive body represented by the constants $R_1$ and $C_1$ where electrolyte decay normally occurs, polarization hardly occurs at the frequency above that for the point B of FIG. 6, so that such boundaries are protected against the above-mentioned adverse effects even when being heated quickly. The AC voltage is applied at a frequency which is sufficiently high that the impedance between the electrodes to which the AC voltage is applied is largely independent of the interface capacitances between those electrodes and the surface of the resistive body.

Moreover, the impedance along the arcuate locus from the point B to the point C is determined by the characteristics of the solid electrolyte per se, so that the locus is hardly affected by the surface conditions of resistive body, the manner in which the electrodes are mounted on the resistive body, the kind of electrodes used, and the changes thereof with elapse of time. Accordingly, when an AC voltage of the frequency higher than that for the point B of FIG. 6 is used, the impedance of the resistive body becomes smaller than the DC resistance of the resistive body, so that stable heating of the solid electrolyte at a comparatively low voltage becomes possible. To prevent localized heating, even if the frequency higher than that for the point B of FIG. 6 is used, it is preferable to select such frequencies which make the reactance due to the capacitance component $C_2$ of FIG. 5 smaller than the resistance component $R_2$.

Figure 7:
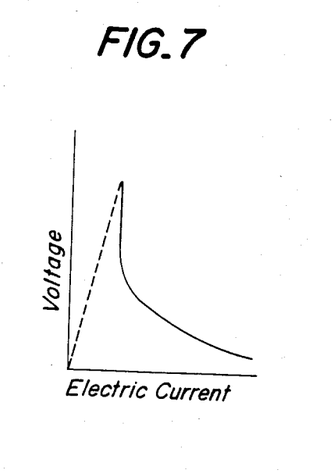
FIG. 7 is a graph showing the relationship between the voltage and the current through the resistive body.

FIG. 7 shows the relationship between the AC current through the resistive body and the AC voltage across the resistive body, provided that the frequency of the AC voltage applied across the electrodes of the resistive body is higher than that for the point B of FIG. 6. In FIG. 7, when the AC current is larger than a certain value, negative co-relation appears between the AC current and the AC voltage, namely, the voltage decreases with the increase of the current as shown by the curve a. This phenomenon is due to the temperature adjusting ability of the resistive body which ability is activated when the resistive body is heated by the alternating current as will be explained hereinafter by referring to FIG. 18. The negative co-relation can be advantageously used, because if the frequency and the amplitude of the alternating current for heating the resistive body are selected in the negative co-relation range of the curve a of FIG. 7, the AC voltage across the resistive body is reduced in response to the flow of the alternative current depending on the temperature of the resistive body reached by the self-heating effect thereof.

Figure 8:
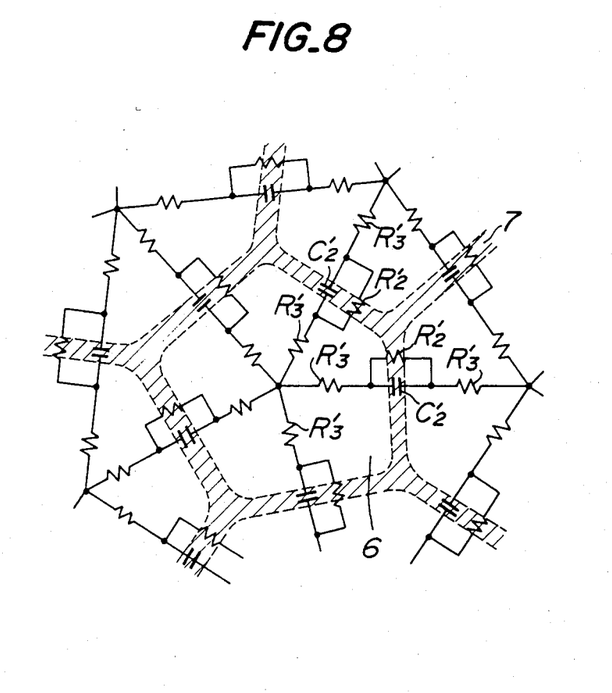
FIG. 8 is a diagrammatic illustration of an equivalent circuit of the microscopic structure of the resistive body including the fine grains or thin films having negative temperature coefficient of electric resistance and high-resistance substance layers.

The resistance components $R_2$ and $R_3$ and the capacitance component $C_2$ in the electrical equivalent circuit of FIG. 5 do not represent concentrated constants but represented distributed constants as illustrated in the enlarged schematic diagram of FIG. 8. More particularly, the constants are substantially uniformly distributed in the resistive body including the fine grains 6 or thin films 9 with the NTCR and the high-resistance substance layers 7 or 7A, so that even when the temperature of one distributed resistance component $R'_3$ increases due to some reasons and the resistance value thereof is reduced to allow an increase of the current therethrough, the current $i'$ therethrough is limited by the distributed capacitance component $C'_2$ in series to the distributed resistance component $R'_3$ and the voltage $V'$ applied to capacitance component $C'_2$ and the frequency f, i.e., at $i'=2\pi fC'_2V$. The voltage $V'$ applied across one portion of the high-resistance substance layer 7 and the distributed capacitance component $C'_2$ are both very small, so that local concentration of the electric current is prevented. Accordingly, with the present invention, the entire resistive body can be uniformly heated without any localized heating even if the resistive body is of plate-like shape and the electrodes are mounted on the opposite surfaces of the plate-like resistive body. On the other hand, the localized heating has been experienced by the conventional heating, such as the heating by simple application of a direct current to a solid electrolyte or by application of an alternating current of a low frequency in a range corresponding to that between the point A and the point B of FIG. 6.

In the oxygen concentration detector of FIG. 4, the temperature of the oxygen concentration cell is accurately measured by determining the impedance of the oxygen concentration cell from the current fed from the AC power source 15 to the oxygen concentration cell as detected by the AC voltage detector 19 detecting the voltage across the current-detecting resistor 16. This temperature measurement through the detection of the impedance will be explained now.

Figure 9:
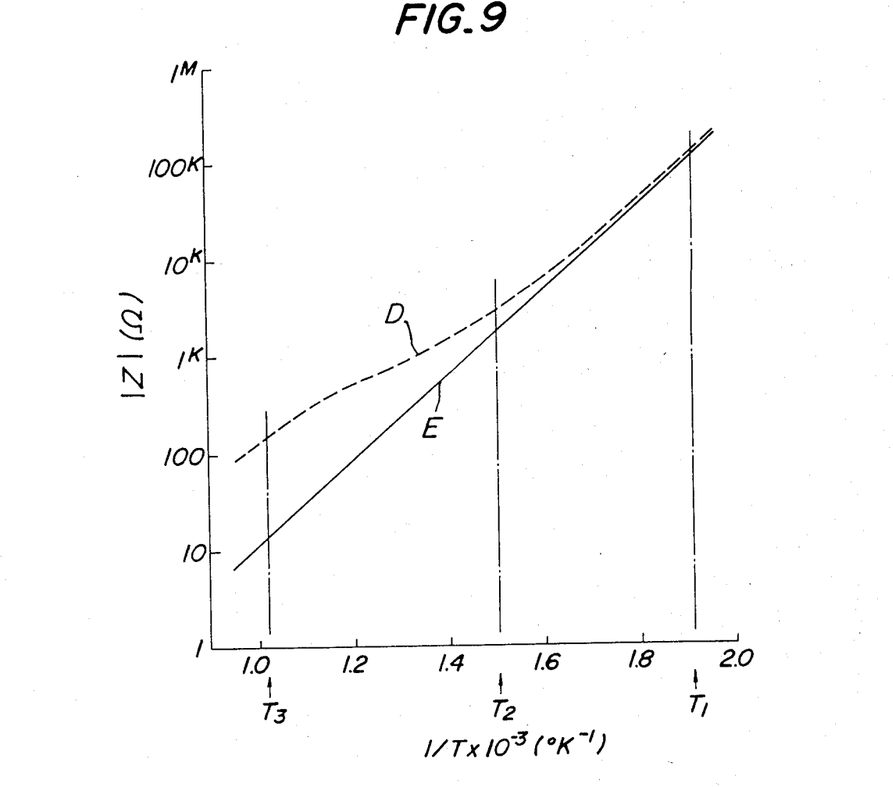
FIG. 9 is a graph showing the relationship between the temperature and the impedance of the resistive body.

The complex impedance characteristics of the resistive body varies with the temperature of the resistive body, and as the temperature increases, the impedance values at the points A, B, and C of FIG. 6 decrease and the frequencies in the proximity of the points B and C increase. FIG. 9 shows the relationship between the temperature of the resistive body and the impedance thereof for fixed frequencies. As can be seen from the figure, the temperature of the resistive body or the solid electrolyte can be determined by measuring the impedance thereof. The dashed line curve D of FIG. 9 shows the result of measurement taken by applying alternating current of that frequency which gives the impedance of the point B of FIG. 6 at the temperature $T_2$, while the solid line curve E shows the result of measurement taken by applying alternating current of that frequency which gives the impedance of the point C of FIG. 6 at the temperature $T_3$.

To measure the impedance, the present invention uses the AC frequency higher than that for the point B of FIG. 6, namely that frequency which causes most of the AC polarization to occur in the inside of the resistive body, as in the case of the AC frequency for heating the resistive body. The reason for using such AC frequency is in that, referring to the dashed line curve D of FIG. 9 using the frequency of the point B of FIG. 6, if the temperature increases from $T_2$ to $T_3$, the impedance varies from the point B of FIG. 6 to the point A thereof, and impedance in the region between the points A and B is considerably affected by properties of the electrodes themselves and the properties of the boundary between the electrodes and the resistive body. Besides, the impedance in this region is very unstable for the purpose of using the resistive body over a long period of time.

Figure 10:
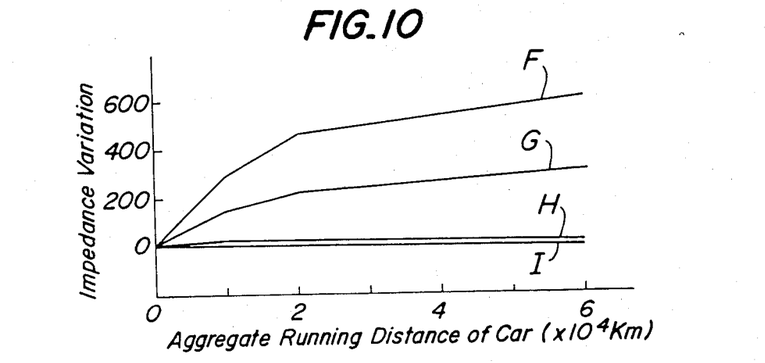
FIG. 10 is a graph showing the change of the impedance of the resistive body used in an oxygen concentration detector which is mounted on an automobile and the aggregate running distance of the automobile.

On the other hand, when the above-mentioned AC frequency higher than that for the point B of FIG. 6, namely that frequency which causes most of the AC polarization to occur in the inside of the resistive body, is used, the impedance is stable unless changes occur in the crystal structure or the grain boundary of the resistive body and such stability of the impedance is maintained even after a long period of use. It is more preferable to use the AC frequency in the proximity of that for the point C of FIG. 6, namely that AC frequency at which the impedance of the resistive body depends only on the crystal structure of the resistive body. FIG. 10 clearly shows the advantages of such frequency by illustrating the variation of the impedance of the oxygen concentration detector at 400° C. with the increase of the aggregate running distance of a car carrying the oxygen concentration detector. In FIG. 10, the curve F is for DC or the frequency for the point A of FIG. 6, the curve G is for the frequency for about the middle point of the arcuate locus between the points A and B of FIG. 6, the curve H is for the frequency for the point B of FIG. 6, and the curve I is for the frequency for the proximity of the point C of FIG. 6. The curves H and I for that frequency which causes most of the AC polarization to occur in the inside of the resistive body are highly stable even after a long period of use.

The determination of the temperature of the resistive body by measuring the impedance thereof has advantages in the elimination of the time lag and the accuracy in the determination of the actual temperature.

Figure 11:
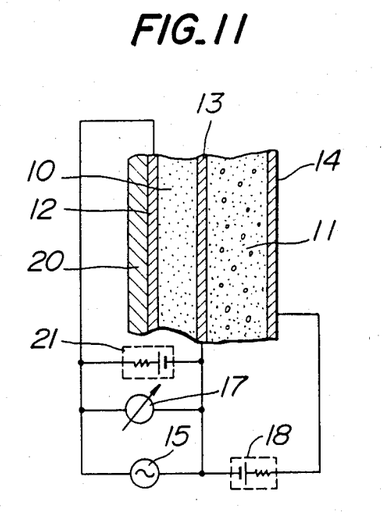
FIGS. 11, 12, 19 and 20 show schematic diagrams of different embodiments of the oxygen concentration detector according to the present invention.

FIG. 11 shows another embodiment of the invention. In this embodiment, a shielding layer 20 made of porous ceramics such as zirconia and spinel is provided on the reference electrode 12, and a DC power source 21 is connected to the oxygen concentration cell made of the resistive body 10. In response to a direct current from the reference electrode 12 to the measuring electrode 13, oxygen ions move from the measuring electrode 13 to the reference electrode 12 where the oxygen ions are converted into oxygen molecules by the following reaction.

$$2(O^{--}) - 4e \rightarrow O_2$$

The shielding layer 20 acts to prevent the thus generated oxygen molecules from leaking to the outside, so that the reference electrode 12 is rendered to have a substantially 100% oxygen concentration and to act for the oxygen concentration cell of the resistive body 10. Accordingly, the conventional arrangement for exposing the reference electrode 12 to the open atmosphere is dispensed with, so that the structure of the oxygen concentration detector is simplified.

Figure 12:
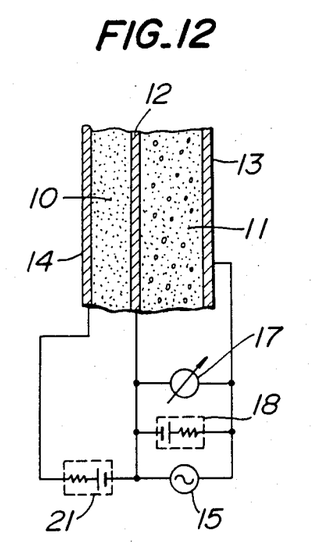
Figure 13:
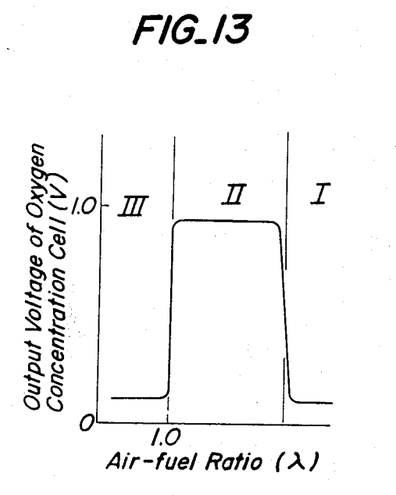
FIG. 13 is a graph showing the relationship between the output terminal voltage of an oxygen concentration cell in the oxygen concentration detector of FIG. 12 and the air-fuel ratio of a gas being measured thereby.

FIG. 12 shows another embodiment of the invention, in which the porous resistive body 11 formed of solid electrolyte is used as an oxygen concentration cell, and a direct current is applied to the oxygen concentration cell. With the arrangement of FIG. 12, the output voltage across the oxygen concentration cell has two sudden changes as shown in FIG. 13. More particularly, the DC power sources 18 and 21 cause the oxygen ions at the reference electrode 12 to emanate from both the measuring electrode 13 and the outer electrode 14 as oxygen into the gas being measured. On the other hand, the oxygen in the gas being measured diffuses through the porous resistive body 11 depending on the difference of oxygen concentration between the measuring electrode 13 and the reference electrode 12, and an equilibrium of oxygen concentration distribution is reached in which the oxygen concentration at the measuring electrode 13 is high while oxygen concentration at the reference electrode 12 is low. For the region I of FIG. 13, wherein the gas being measured contains a considerably high oxygen concentration, both the measuring electrode 13 and the reference electrode 12 are under the conditions of excess oxygen, so that the electromotive force is low. For the region II, wherein the oxygen concentration of the gas being measured is lower than that in the region I, the reference electrode 12 becomes deficient oxygen condition while the measuring electrode 13 becomes excess oxygen condition, so that an electromotive force of about 1 V is produced. For the region III, both the measuring electrode 13 and the reference electrode 12 become deficient oxygen condition, and the electromotive force becomes low. In the embodiment of FIG. 12, the reference electrode 12 provides a reference and the shielding layer 20 of FIG. 11 can be dispensed with.

Figure 14:
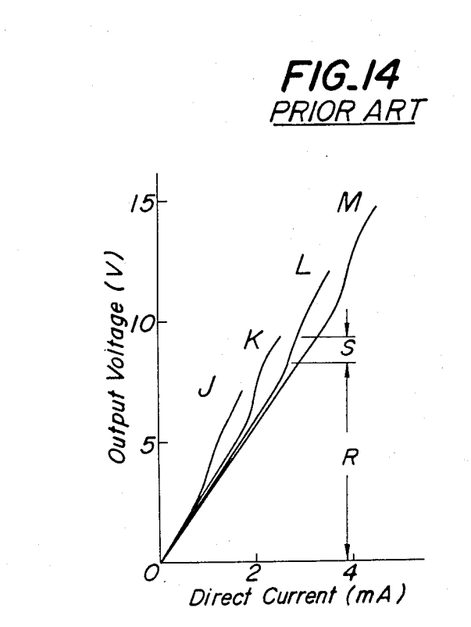
FIGS. 14 through 17 are graphs showing the variation of the voltage across the output terminals of the oxygen concentration cell when a direct current is applied therethrough.
Figure 15:
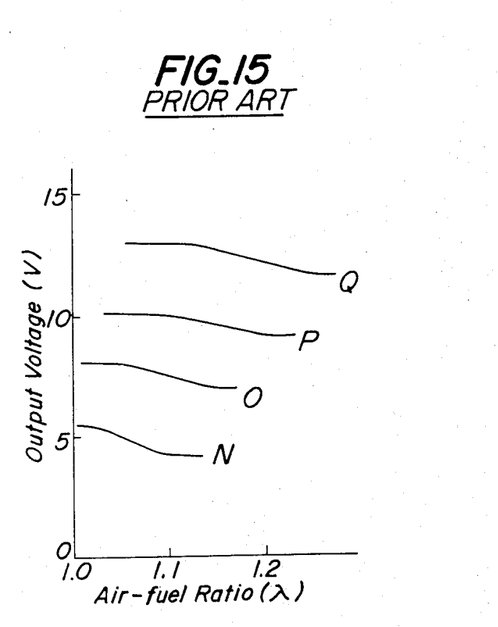
Figure 16:
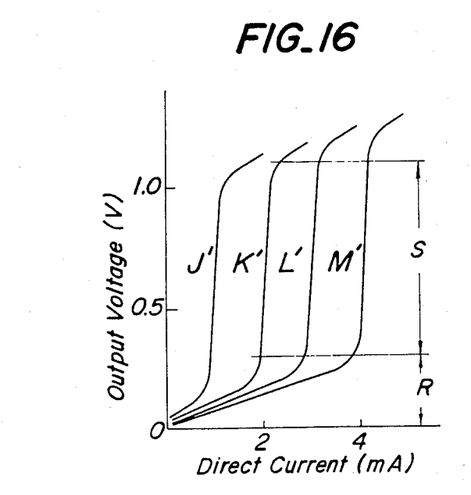
Figure 17:
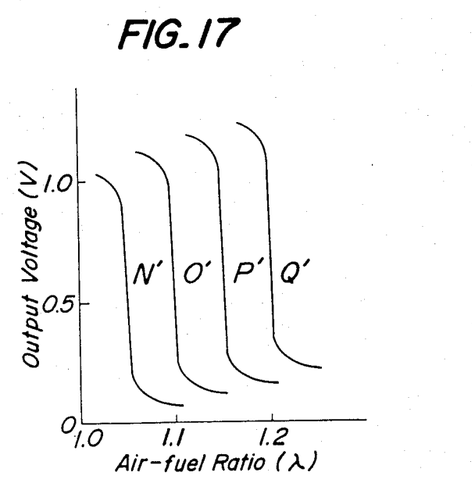

In the embodiments of FIG. 11 and FIG. 12, a direct current flows through the oxygen concentration cell of the oxygen concentration detector. However, since the oxygen concentration cell is heated, the polarization in the oxygen concentration cell due to the direct current is very low and such polarization can be neglected as compared with the electromotive force of the oxygen concentration cell. More particularly, FIG. 14 through FIG. 17 show the output voltage of the oxygen concentration cell for the exhaust gas of about 450° C.: namely, FIG. 14 and FIG. 15 give current vs. output voltage curves and air-fuel ratio vs. output voltage curves for a conventional oxygen concentration cell without AC heating, while FIG. 16 and FIG. 17 give current vs. output voltage curve and air-fuel ratio vs. output voltage curves for the oxygen concentration cell which is heated by the AC voltage as shown in FIGS. 11 and 12. The curves J, K, L, and M of FIG. 14 and the curves J', K', L', and M' of FIG. 16 show the relationship between the direct current and the output voltage of the oxygen concentration cell for exhaust gases having oxygen concentrations of 1%, 2%, 3%, and 4%, respectively. The curves N, O, P, and Q of FIG. 15 and the curves N', O', P', and Q' of FIG. 17 show the relationship between the air-fuel ratio λ and the output voltage (V) of the oxygen concentration cell for direct currents of 1 mA, 2 mA, 3 mA, and 4 mA, respectively. The air-fuel ratio λ of 1.1 corresponds to an oxygen concentration of about 2% in the exhaust gas, and λ=1.2 corresponds to about 4% oxygen concentration. As can be seen from FIG. 14 and FIG. 16, with increase of the direct current, the output voltage of the oxygen concentration cell suddenly increases in a step-like fashion at certain values of the direct current, and the increment of such step-like increase as represented by the symbol S in FIG. 14 and FIG. 16 is about 1 V irrespectively of heated or not. Such increment substantially corresponds to the electromotive force of the oxygen concentration cell. The value of that direct current at which the output voltage of the oxygen concentration cell changes in a step-like fashion depends on the oxygen concentration in the exhaust gas and the structure of the diffusion layer. In the case of FIGS. 14 and 16, if the oxygen concentration is 2%, the step-like change of the output voltage occurs at 2 mA of the direct current as shown by the curves K and K'. In the case of the conventional oxygen concentration cell without heating as shown in FIG. 14, the value of the polarization R due to the direct current through the oxygen concentration cell is several volts to over 10 V, which is large as compared with the step-like change S of about 1 V. Besides, the value of the polarization R varies considerably depending on the temperature of the exhaust gas. Accordingly, it has been difficult to detect the air-fuel ratio λ from the output voltage of the oxygen concentration cell including both the large polarization R due to the direct current and the step-like change S. The operating conditions which allow such a large polarization R tend to cause chipping of the electrodes and the chemical change of the solid electrolyte, so that long service life could not be expected. On the other hand, in the case of the heated oxygen concentration detector according to the present invention as shown in FIG. 16, the step-like change S is about 1 V which is substantially the same as that of the prior art, while the polarization R due to the direct current through the oxygen concentration cell is 0.2 to 0.3 V and hardly affected by the temperature of the exhaust gas, and such polarization is negligible as compared with the step-like change S or the electromotive force of the oxygen concentration cell. Besides, in the detector of the invention, the direct current through the oxygen concentration cell does not cause any adverse effects on the electrodes and the solid electrolyte. As regards the output voltage change characteristics for the air-fuel ratio λ, the oxygen concentration detector of the invention provides step-like change of the output voltage from about 0.3 V to about 1 V as shown in FIG. 17, so that the air-fuel ratio λ can be controlled accurately and easily for instance by selecting a reference value at the output voltage of 0.6 V.

Figure 18:
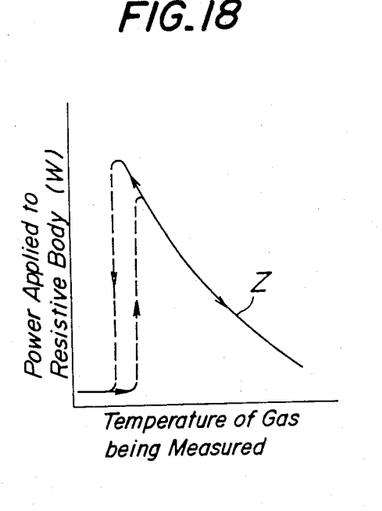
FIG. 18 is an explanatory diagram of the temperature self-control characteristics of the oxygen concentration detector of the invention.

In the embodiment of FIG. 4, the current-detecting resistor 16 carries out not only the detection of the impedance but also the prevention of the current through the resistive body 10 from increasing excessively. Besides, when the resistive body 10 is hot and further heating is not necessary, the current-detecting resistor 16 also suppresses the power to the resistive body 10. The curve Z of FIG. 18 shows the negative characteristics of the relationship between the temperature of the gas being measured and the power applied to the resistive body, and if the negative characteristics portion of the curve Z is used, temperature self-control property is rendered to the resistive body, so that the width of temperature change of the resistive body 10 can be made narrower than the width of temperature change of the gas being measured. Whereby the temperature correction of the electromotive force of the oxygen concentration cell is made accurate and easy. Besides, fluctuation of the diffusion speed of oxygen in the porous resistive body 11 of FIG. 4 and FIG. 12 for temperature changes can be minimized, and the temperature correction thereof is made easy even if required. The current-detecting resistor 16 of FIG. 4 can be replaced with a capacitor or a coil, and separate elements may be used for the current detection and the current limitation.

The AC voltage for heating should be applied to the solid electrolyte acting as an oxygen concentration cell, but the AC voltage for the impedance detection may be applied to a resistive body which is different from the solid electrolyte acting as an oxygen concentration cell. Separate AC power sources may be used for the heating and for the impedance detection, and in such a case, the frequencies of such AC power sources my be the same or different from each other.

The shape of the solid electrolyte or the resistive body to be used in the oxygen concentration detector of the present invention can be plate-like, cylinder-like, cylinder-like with a bottom, or thin-film-like. The solid electrolyte capable of self-heating may be provided with a portion which is thinner than the remaining portions thereof, so that such thin portion may be made hottest in the solid electrolyte, and if such thin portion is disposed adjacent to the oxygen concentration cell with which the exhaust gas is easily brought into contact, the sensitivity and the response of the oxygen concentration detector are both improved.

Figure 19:
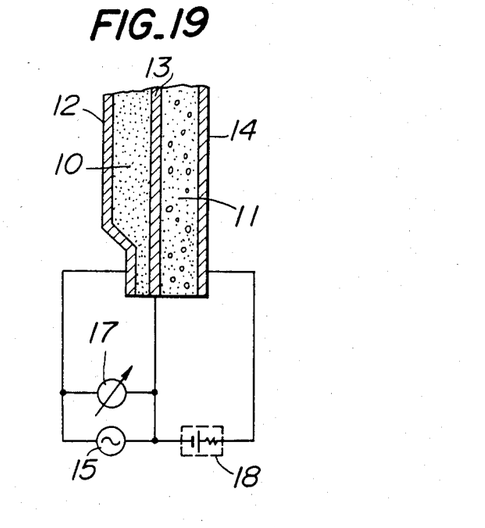

FIG. 19 shows an embodiment which has the tip portion of the resistive body 10 consisting of solid electrolyte made thin, so as to cause local self-heating at the thin portion. Besides, a direct current is applied to the thin portion, so as to control that value of the air-fuel ratio λ at which the electromotive force of the oxygen concentration cell is suddenly changed. In this embodiment, the porosity of the resistive body 11 must be uniform only at the portion adjacent to the self-heating thin portion of the resistive body 10, whereby the steep change of the electromotive force is ensured in the oxygen concentration detector. More particularly, in conventional oxygen concentration detectors, if the thickness of the diffusion layer is uneven, the diffusion speed of oxygen therethrough becomes uneven, so that a difference is produced between the magnitude of the sudden change in the electromotive force at the thick portion and the magnitude of the sudden change in the electromotive force at the thin portion, whereby the steepness of the overall sudden change of the electromotive force is lost. On the other hand, if the heating is caused at a certain localized portion, only such localized portion acts as the main oxygen concentration cell, so that it is sufficient to keep the thickness uniformity of the diffusion layer at such localized portion. Preferably, the diffusion layer for the non-heated portion is made thicker than that for the heated localized portion, or that part of the electrode which faces the non-heated portion of the solid electrolyte is coated with an airtight layer. Even if the heated portion is localized, the present invention determines the temperature of the resistive body or the solid electrolyte by detecting the impedance thereof, so that the temperature of the heated portion or the portion acting as an oxygen concentration cell can be accurately measured.

It should be noted here that the temperature of the solid electrolyte can be kept constant by feeding back the voltage across the current-detecting resistor 16 for impedance detection to the circuit of the AC power source 15 for heating so as to control the electric power applied to the solid electrolyte through regulation of the voltage or frequency of the AC power source 15. The detection of the impedance is preferably carried out at the solid electrolyte forming the oxygen concentration cell as shown in FIG. 4, because such detection is direct, but it is also possible to detect at the resistive body 11 of FIG. 11 or at a resistive body separately provided therefor. To ensure good temperature follow-up of such separate resistive body for impedance detection, the heat capacity of the separate resistive body must be minimized for instance by making the separate resistive body thinner than the solid electrolyte forming the oxygen concentration cell. The function of the reference electrode 12 as the reference can be maintained even if a porous resistive body layer is added between shielding layer 20 and the reference electrode 12 of FIG. 11, or even if separate reference electrodes 12 are provided to the solid electrolytes 10 and 11 as shown in FIG. 12 and a porous resistive body layer is added to such separate reference electrodes 12.

The arrangement of the solid electrolyte, the resistive bodies, the diffusion layers, and the porous resisitive bodies is not limited to those which are illustrated in FIG. 4, FIG. 11, FIG. 12, and FIG. 19. In fact, the position, the number, and the magnitude thereof can be selected so as to meet various requirements of specific use. As to the methods of securing the electrodes, FIG. 20 shows an arrangement in which electrodes or heating and electrodes for detecting the electromotive force are separated but mounted on one resistive body 10 made of solid electrolyte, so as to use the resistive body 10 for two purposes, namely heating and generating electric potential.

The invention will be described in further detail by referring to an example.

EXAMPLE

Figures 20, 21:
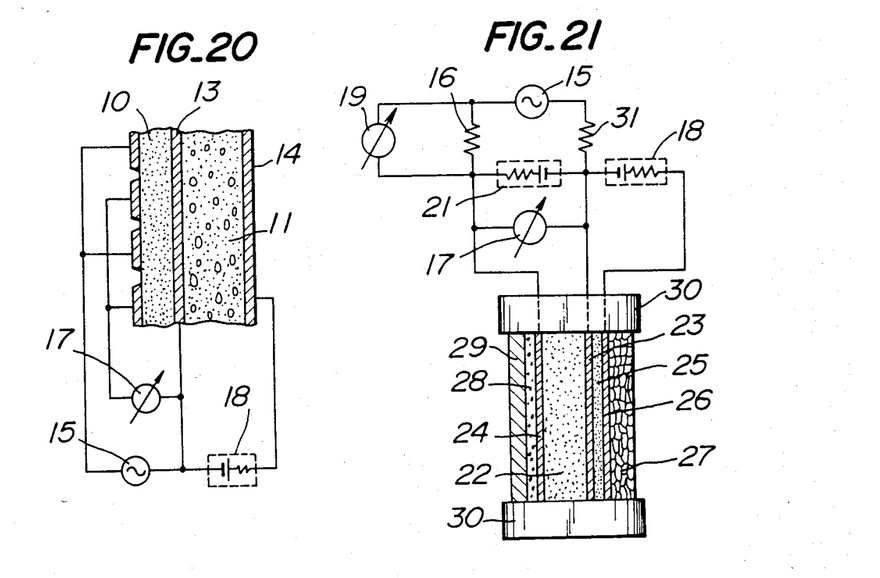
FIG. 21 is an explanatory diagram of an oxygen concentration detector which was tested as an example of the present invention.

Referring to FIG. 21, a disk-shaped solid electrolyte 22 with an outer diameter of 5 mm and a thickness of 0.3 mm was prepared by using zirconia ($ZrO_2$) porcelain consisting of 100 parts of a mixture of 95 mol % zirconia ($ZrO_2$) and 5 mol % yttria ($Y_2O_3$) and 3 parts of clay. An oxygen concentration cell was formed by mounting platinum electrodes 23 and 23 on opposite surfaces of the solid electrolyte 22. A porous disk-shaped solid electrolyte 25 with an outer diameter of 5 mm and a thickness of 0.1 mm was prepared by using similar zirconia ($ZrO_2$) porcelain consisting of 100 parts of the mixture of 95 mol % zirconia ($ZrO_2$) and 5 mol % yttria ($Y_2O_3$) and 3 parts of clay, and this porous solid electrolyte 25 was tightly secured to the platinum electrode 23. Another platinum electrode 26 was secured to the porous solid electrolyte 25, and a protective layer 27 of alumina spinel was applied to the platinum electrode 26. On the other hand, a porous layer 28 consisting of alumina spinel was applied to the surface of the platinum electrode 24, and a porous protective layer 29 made of spinel was coated on the porous layer 28. The thus assembled body was placed in an alumina ($Al_2O_3$) porcelain case 30.

An AC power source 15 with a 30 kHz output voltage of 30 V with rectangular waveform was connected across the solid electrolyte 22 through a current-detecting resistor 16 and a current-limiting resistor 31. A DC power source 18 was connected across the solid electrolyte 25, so as to cause movement of oxygen from the electrode 23 of the solid electrolyte 25 to the other electrode 26 thereof. Another DC power source 21 was connected across the oxygen concentration cell forming solid electrolyte 22, so as to cause movement of oxygen from the electrode 23 to the other electrode 24, said DC current being capable of being simultaneously applied across the solid electrolyte 22 with the AC power source 15. A DC voltage detector 17 was connected across the solid electrolyte 22, so as to detect the electromotive force of the oxygen concentration cell, thereby producing an example of an oxygen concentration detector of the invention. The oxygen concentration detector thus produced was placed in an engine exhaust gas system at about 250° C. with known levels of air-gas ratio λ. The current from the DC power source 18 was set at 2 mA, and the current from the DC power source 21 was set at 0.2 mA. The response of the elecromotive force of the oxygen concentration detector was measured by changing the air-fuel ratio λ from 1.0 to 1.2.

For reference, measurements were also taken without applying AC heating. The current-limiting resistor 31 has a resistance of 300 Ω, and the response speed of the oxygen concentration detector was determined by measuring the time necessary for changing the electromotive force from 600 mV to 300 mV.

The result of the measurement showed that the response speed was 80 msec, and that in the case of measurement without heating the voltage of the DC power source 18 became more than 120 V and cracks were formed on the solid electrolyte 25 and the response speed could not be measured.

Figure 22:
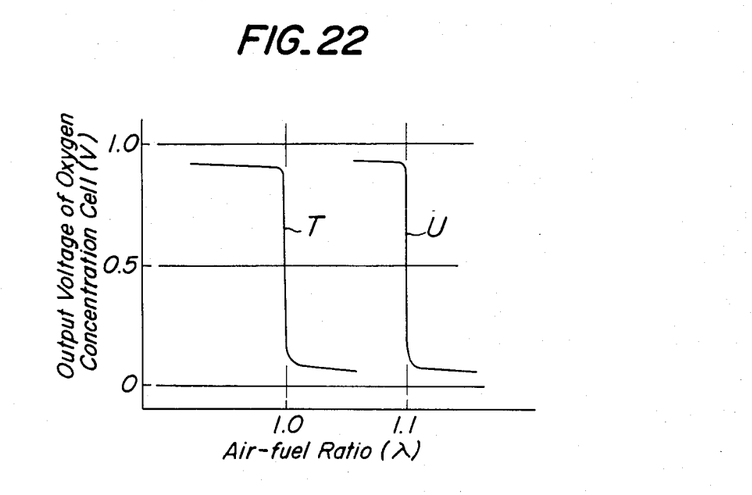
FIGS. 22 and 23 are graphs showing the results of tests which were conducted on the example of FIG. 22.

The output voltage of the oxygen concentration cell of the oxygen concentration detector was measured when the air-fuel ratio λ was changed while maintaining other conditions of the engine exhaust gas system constant, for both with and without the current from the DC power source 18. The result is shown in FIG. 22, wherein the curve U is for the case with the direct current and the curve T is for the case without the direct current. The tests proved the fact that the change of the electromotive force was steep even at low temperatures and the steepness of such change of electromotive force was not affected by the application of the direct current.

The temperature of the solid electrolyte 22 was determined by measuring the impedance of the solid electrolyte 22 forming the oxygen concentration cell by changing the temperature of the exhaust gas in three steps i.e., 250° C., 450° C., and 650° C., while using the above-mentioned engine exhaust gas system and samples and keeping the air-fuel ratio λ at 0.9. At the same time, the power applied to the solid electrolyte and the electromotive force of the oxygen concentration cell were measured. For reference, measurement was taken on a conventional oxygen concentration detector having a thermistor temperature detecting element disposed in a cylindrical solid electrolyte with a bottom. The result is shown in Table 1.

TABLE 1

| Exhaust gas temperature (°C.) | Art | Impedance of solid electrolyte (Ω) | Temperature determined by impedance (°C.) | Temperature of solid electrolyte directly measured (°C.) | Power applied to solid electrolyte (W) | Output voltage (V) |
|---|---|---|---|---|---|---|
| 250 | The | 36 | 520 | 522 | 3.9 | 0.90 |
| 450 | invention | 12 | 560 | 558 | 1.7 | 0.90 |
| 650 |  | 2.5 | 660 | 665 | 0.3 | 0.89 |
| 250 | Prior art |  |  | 240 |  | 0.73 |
| 450 |  |  |  | 438 |  | 0.90 |
| 650 |  |  |  | 635 |  | 0.89 |

As shown in Table 1, the solid electrolyte temperature as determined by the impedance was in good agreement with the temperature thereof directly measured. For the variations of the exhaust gas temperature, the temperature change of the solid electrolyte was about one third.

The direct measurement of the solid electrolyte was carried out by boring a hole of 0.3 mm diameter from the surface of the shielding layer 29 to about the center of the solid electrolyte 22, inserting a thermocouple in this hole, filling an inorganic adhesive in the gap between the thermocouple and the diffusion layer, and measuring the electromotive force of the thermocouple.

Thereafter, the engine rotating speed was suddenly raised from 1,000 rpm to 4,000 rpm while keeping the air-fuel ratio λ of the engine exhaust gas system at 1.1, and the temperature change of the exhaust gas was measured, and simultaneously the temperature change of the solid electrolyte was determined by measuring the impedance variation while applying the direct current. For reference, measurement was taken on a conventional oxygen concentration detector having a thermistor temperature detecting element disposed in a cylindrical solid electrolyte with a bottom.

Figure 23:
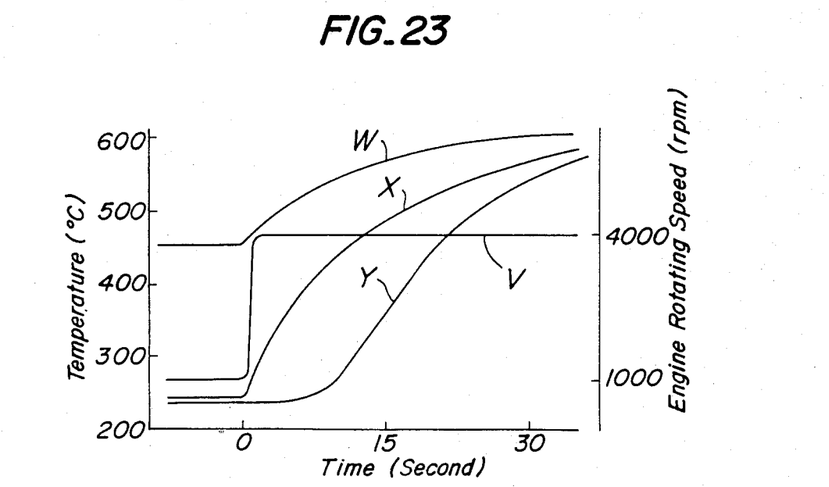

The result of the measurements is shown in FIG. 23, wherein the curve V shows the variation of the rotating speed, the curve W shows the temperature variation of the solid electrolyte measured by the impedance, the curve X shows the variation of the exhaust gas temperature, and the curve Y shows the temperature change of the solid electrolyte as determined by the conventional thermistor temperature detecting element.

As can be seen from FIG. 23, when the engine rotating speed suddenly changed, the temperature of the exhaust gas increased along the curve X and the temperature of the solid electrolyte also increased, and the curve W showing the temperature change of the solid electrolyte measured by the impedance according to the present invention did not have any substantial time lag relative to the exhaust gas temperature change of the curve X. On the other hand, the curve Y showing the temperature change of the solid electrolyte measured by the conventional thermistor had a considerably large time lag relative to the curve X showing the temperature change of the exhaust gas, so that the measurement by the thermistor was apparently inaccurate for the purpose of temperature correction of the electromotive force of the solid electrolyte and the temperature correction of the diffusion speed of the diffusion layer in response to the variation of the exhaust gas.

As described in the foregoing, in the oxygen concentration detector according to the present invention, the solid electrolyte is self-heated in a stable fashion over a long period of time by applying a comparatively low AC voltage thereto, so that oxygen concentration of exhaust can be detected with a quick response even if the temperature of the exhaust gas is low. Even when the output voltage of the oxygen concentration cell is low, deposition of carbon or the like on the porous solid electrolyte or the diffusion layer is minimized. That value of the air-fuel ratio λ at which the electromotive force of the oxygen concentration cell varies suddenly can be accurately controlled to the lean burn zone or to the rich burn zone by applying a direct current, without requiring exposure of the reference electrode to the open atmosphere. Besides, the temperature of the solid electrolyte can be accurately measured without any time lag over a long period of use. In the present invention, local heating of the solid electrolyte can be easily carried out, so as to minimize the electric power for the heating, and the steep sudden change of the electromotive force can be achieved by keeping the uniform thickness of the diffusion layer only at the portion corresponding to the localized heated portion. The self-heating of the solid electrolyte can provide the temperature self-control function, so that even when the temperature of the porous solid electrolyte or the diffusion layer is changed, the change in the diffusion speed is kept small, whereby fluctuation in that air-fuel ratio λ at which the electromotive force changes suddenly due to the change in the diffusion speed is minimized. Thus, the oxygen concentration detector of the present invention has excellent performance in terms of the accuracy, the response, and the durability. As compared with the prior art, the oxygen concentration detector of the present invention does not use any separate temperature detecting element and any heater wire, so that the risk of fault due to the breakage of the heater wire is completely eliminated. Furthermore, the structure of the oxygen concentration detector of the invention is very simple. In short, the present invention provides an oxygen concentration detector which has the above-mentioned advantages and which is particularly suitable for detection of the oxygen concentration in the exhaust gas from internal combustion engines, so that the invention contributes greatly to the industry.

Although the invention has been described with a certain degree of particularly, it is understood that the present disclosure has been made only by way of example and that numerous changes in details of construction and the combination and arrangement of parts may be resorted to without departing from the scope of the invention as hereinafter claimed.

What is claimed is:

1. An oxygen concentration detector for detecting oxygen concentration in gases, comprising:

a plurality of resistive bodies, each of said resistive bodies including a number of portions with a negative temperature coefficient of electric resistance and high-resistance substance layers separating said portions one from the other, and at least two separate electrodes contacting each of said plurality of resistive bodies, each of said resitive bodies being located between said at least two separate electrodes, at least one of said plurality of resistive bodies being a solid electrolyte, thereby forming an oxygen concentration cell, at least another of said plurality of resistive bodies being a solid electrolyte other than said oxygen concentration cell;

an AC power source connected to said at least two separate electrodes contacting said oxygen concentration cell, said AC power source applying an AC current to said oxygen concentration cell so as to heat said cell, said AC power source being arranged to supply an AC voltage at a frequency sufficiently high that an impedance between said at least two electrodes to which AC voltage is applied is largely independent of interface capacitances between said electrodes to which AC voltage is applied and a surface of said concentration cell;

a DC source, said DC source applying a DC current to said electrolyte, for controlling oxygen partial pressure around at least one electrode contacting said oxygen concentration cell; and means for measuring a DC potential difference of the oxygen concentration cell.

2. The detector of claim 1, wherein said portions of said resistive bodies with a negative temperature coefficient of electric resistance are fine grains.

3. The detector of claim 1, wherein said portions of said resistive bodies with a negative temperature coefficient of electric resistance are thin films.

4. The detector of claim 1, wherein an AC current and an AC voltage applied between the electrodes have a negative relation, such that when one increases, the other decreases.

5. The detector of claims 1, 2, 3, or 4, wherein the AC current has a frequency at which an impedance of electrostatic capacitance at highly resistant region layers interposed between the fine grains or thin films is less than a resistance at the highly resistant region layers.

6. The detector of claim 5, further comprising means for detecting an impedance of one of said resistive bodies by applying an AC current therethrough, said AC current having a frequency sufficiently high such that an impedance between said at least two electrodes to which AC voltage is applied is largely independent of interface capacitances between said electrodes to which AC voltage is applied and a surface of said resistive bodies.

7. The detector of claims 1, 2, 3 or 4, further comprising means for detecting an impedance of one of said resistive bodies by applying an AC current therethrough, said AC current having a frequency sufficiently high such that an impedance between said at least two electrodes to which AC voltage is applied is largely independent of interface capacitances between said electrodes to which AC voltage is applied and a surface of said resistive bodies.

8. The detector of claims 1, 2, 3 or 4, further comprising an auxiliary heating means attached to one of said resistive bodies.

9. The detector of claim 1, wherein at least one of said at least two electrodes contacting said oxygen concentration cell is common with at least one electrode of said at least two electrodes contacting said another resistive body.

* * * * *